(12) United States Patent
Alvarado

(10) Patent No.: US 10,743,862 B1
(45) Date of Patent: Aug. 18, 2020

(54) LAPAROSCOPIC SUTURING DEVICE AND METHODS OF USE

(71) Applicant: Alfredo Alvarado, Bogota D.C. (CO)

(72) Inventor: Alfredo Alvarado, Bogota D.C. (CO)

( * ) Notice: Subject to any disclaimer, the term of this patent is extended or adjusted under 35 U.S.C. 154(b) by 66 days.

(21) Appl. No.: 15/897,426

(22) Filed: Feb. 15, 2018

Related U.S. Application Data

(63) Continuation of application No. 14/732,035, filed on Jun. 5, 2015, now abandoned, which is a continuation of application No. 11/418,050, filed on May 4, 2006, now abandoned.

(51) Int. Cl.
  *A61B 17/04* (2006.01)
  *A61B 17/06* (2006.01)
  *A61B 17/00* (2006.01)

(52) U.S. Cl.
  CPC .... *A61B 17/0469* (2013.01); *A61B 17/06066* (2013.01); *A61B 17/06128* (2013.01); *A61B 2017/00367* (2013.01); *A61B 2017/0475* (2013.01); *A61B 2017/061* (2013.01)

(58) Field of Classification Search
  CPC .......... A61B 17/0469; A61B 2017/047; A61B 2017/0472; A61B 2017/0474; A61B 2017/0475; A61B 2017/0477; A61B 2017/0479; A61B 2017/048; A61B 2017/0609; A61B 17/0467; A61B 17/0482; A61B 17/0483; A61B 17/0485; A61B 17/06; A61B 17/0604; A61B 2017/0608
  USPC ....... 606/148, 139, 144, 145, 146, 147, 149, 606/150
  See application file for complete search history.

(56) References Cited

U.S. PATENT DOCUMENTS

| | | | | |
|---|---|---|---|---|
| 2,348,218 A | * | 5/1944 | Karle | A61B 17/0469 606/146 |
| 2,457,379 A | * | 12/1948 | Kallenbach | A61B 17/04 606/146 |
| 5,219,358 A | * | 6/1993 | Bendel | A61B 17/0469 606/139 |
| 5,320,632 A | | 6/1994 | Heidmueller | |
| 5,387,221 A | * | 2/1995 | Bisgaard | A61B 17/0469 112/169 |
| 5,403,328 A | | 4/1995 | Shallman | |
| 5,437,680 A | | 8/1995 | Yoon | |
| 5,454,823 A | | 10/1995 | Richardson | |
| 5,478,344 A | | 12/1995 | Stone | |
| 5,480,406 A | | 1/1996 | Nolan | |

(Continued)

*Primary Examiner* — Wade Miles
*Assistant Examiner* — Kankindi Rwego
(74) *Attorney, Agent, or Firm* — Mark D. Bowen, Esq.; Malin Haley DiMaggio & Bowen, P.A.

(57) ABSTRACT

A laparoscopic suturing device that allows the insertion and formation of intracorporeal knots in a safe and speedy manner during laparoscopic procedures. The laparoscopic suturing device includes an ergonomic handle and a long tubular shaft that contains a connecting rod inside. The proximal end of said connecting rod is attached to a deploying knob and its distal end is linked to a movable needle support that contains a suturing needle. The suturing device is inserted into the gas distended abdominal cavity with the needle in a straight position through a laparoscopic cannula and then by moving backwards said deploying knob the needle is deployed in a right angle allowing the insertion of a variety of sutures. The laparoscopic suturing device is provided with an encasement to keep a spool of suture material in place.

4 Claims, 12 Drawing Sheets

(56) References Cited

U.S. PATENT DOCUMENTS

| | | | |
|---|---|---|---|
| 5,522,820 A | 6/1996 | Caspari | |
| 5,571,119 A | 11/1996 | Atala | |
| 5,674,230 A | 10/1997 | Tovey | |
| 5,690,653 A | 11/1997 | Richardson | |
| 5,707,379 A | 1/1998 | Fleenor | |
| 5,716,369 A | 2/1998 | Riza | |
| 5,728,107 A | 3/1998 | Zlock | |
| 5,728,113 A | 3/1998 | Sherts | |
| 5,797,927 A | 8/1998 | Yoon | |
| 5,860,992 A * | 1/1999 | Daniel | A61B 17/0469 606/139 |
| 5,871,488 A | 2/1999 | Tovey | |
| 5,938,668 A | 8/1999 | Scirica | |
| 5,954,732 A | 9/1999 | Hart | |
| 6,533,795 B1 | 3/2003 | Tran | |
| 6,551,330 B1 | 4/2003 | Bain | |
| 6,554,845 B1 | 4/2003 | Fleenor | |
| 2005/0267529 A1 | 12/2005 | Crockett et al. | |
| 2006/0276835 A1 * | 12/2006 | Uchida | A61B 17/0467 606/205 |
| 2007/0179510 A1 | 8/2007 | Stone | |
| 2010/0318105 A1 * | 12/2010 | Jayant | A61B 17/12013 606/148 |

\* cited by examiner

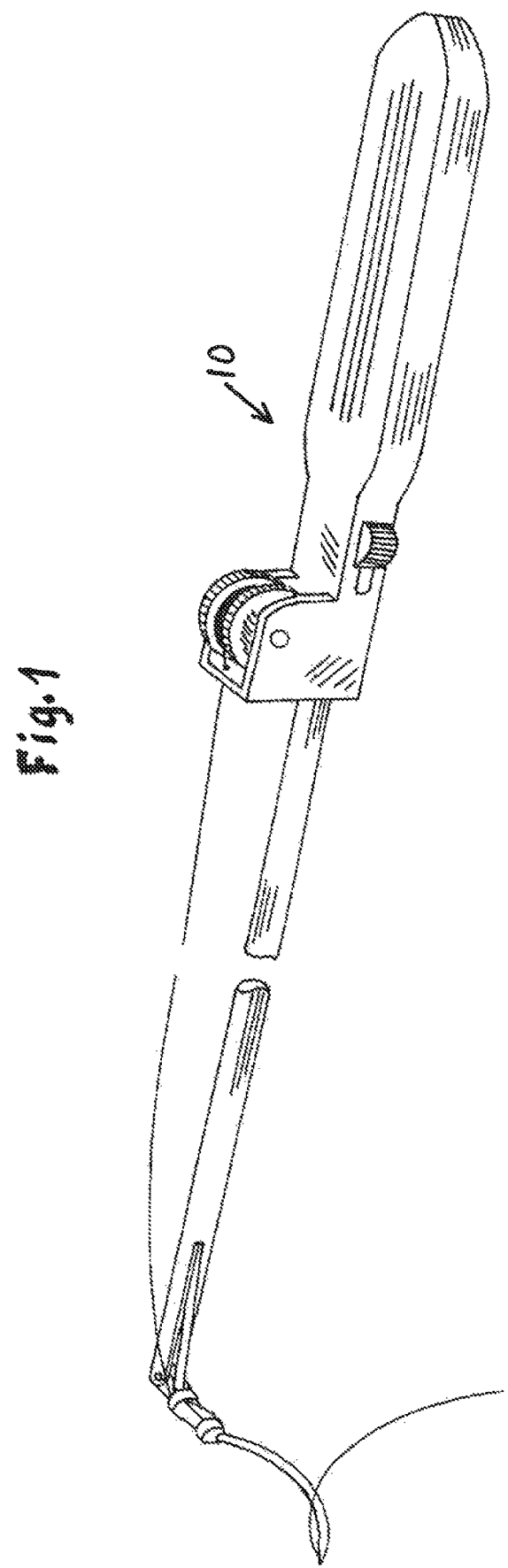

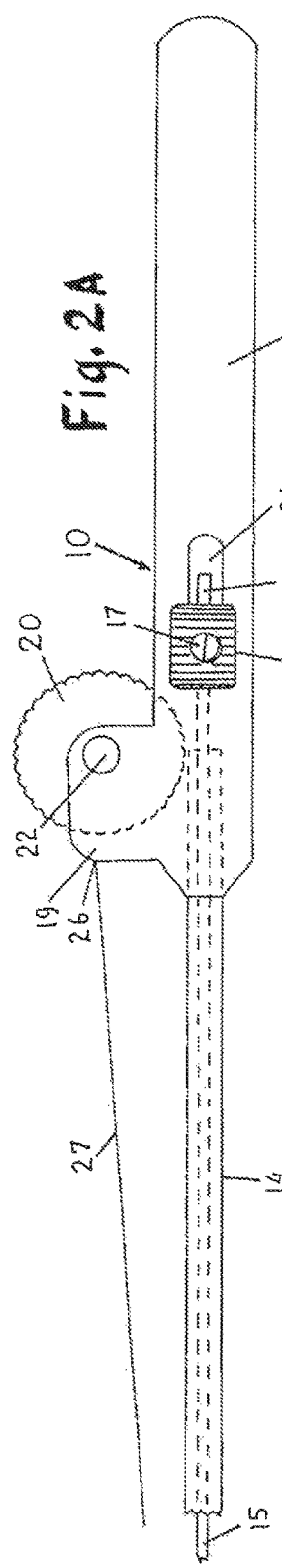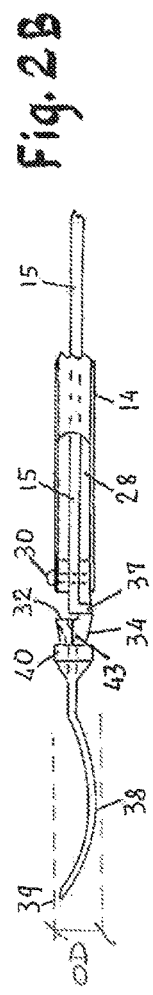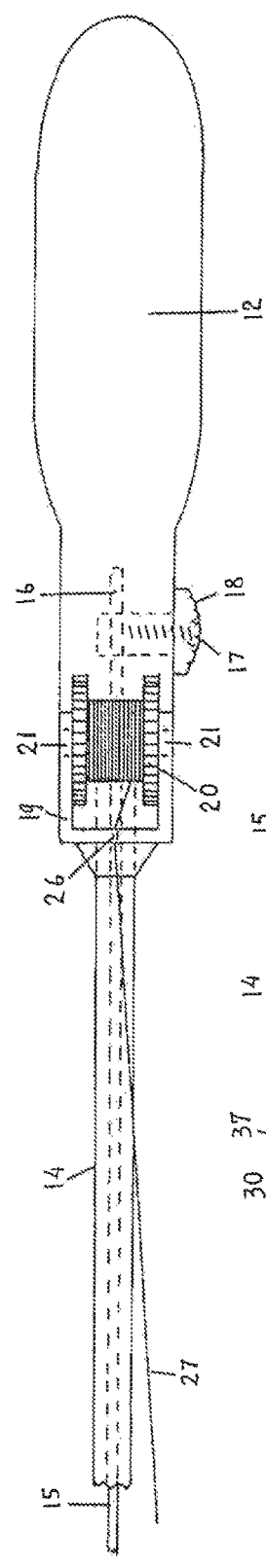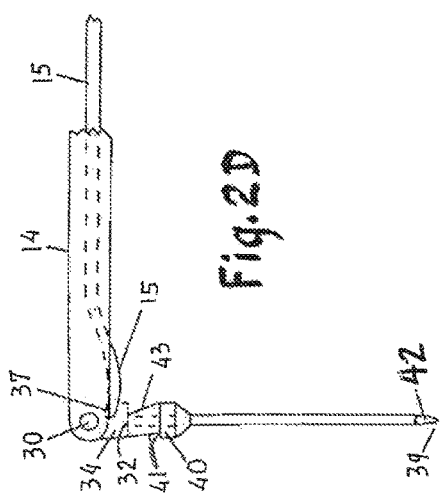

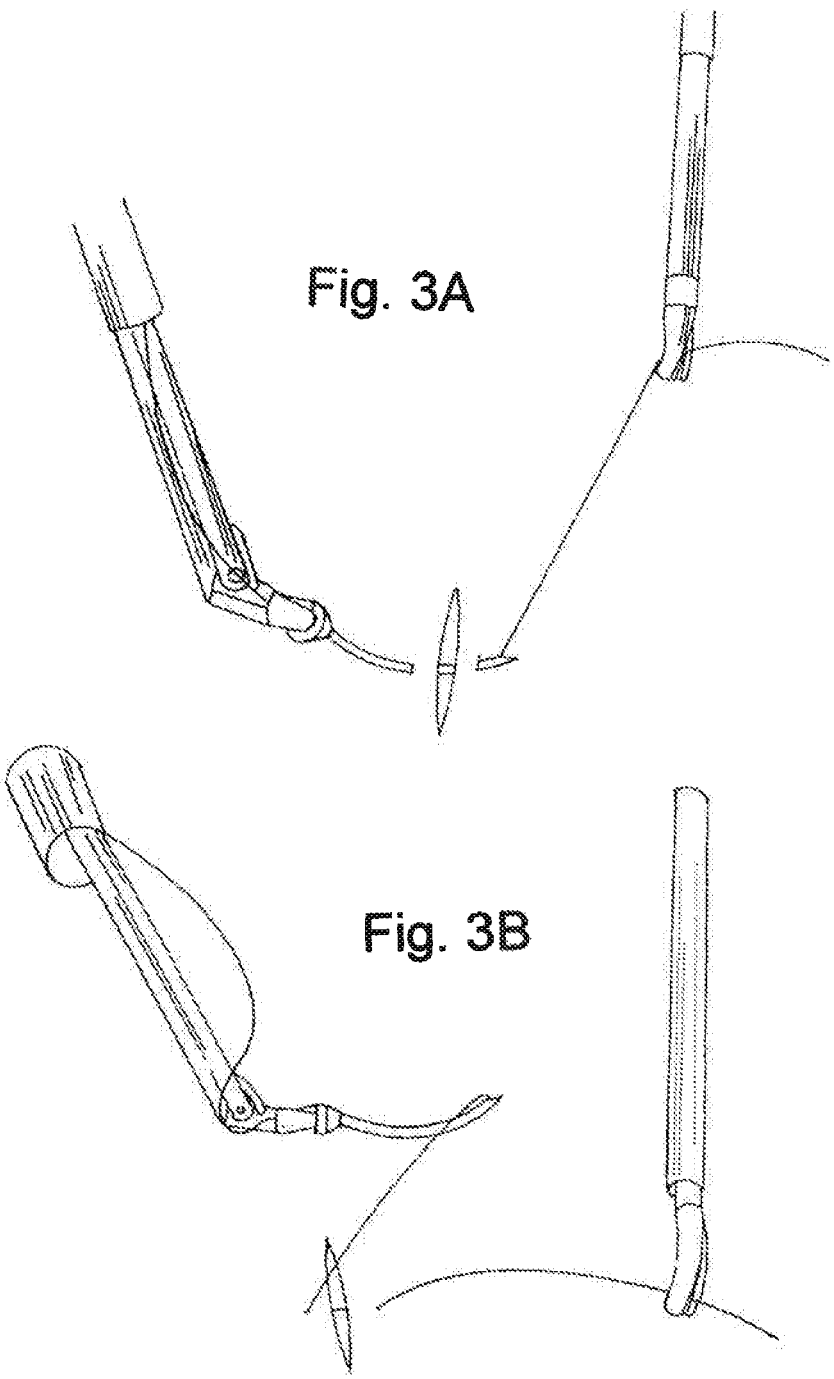

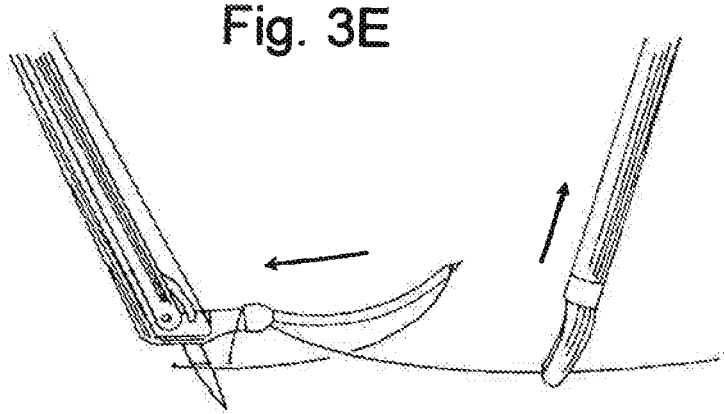
Fig. 3E
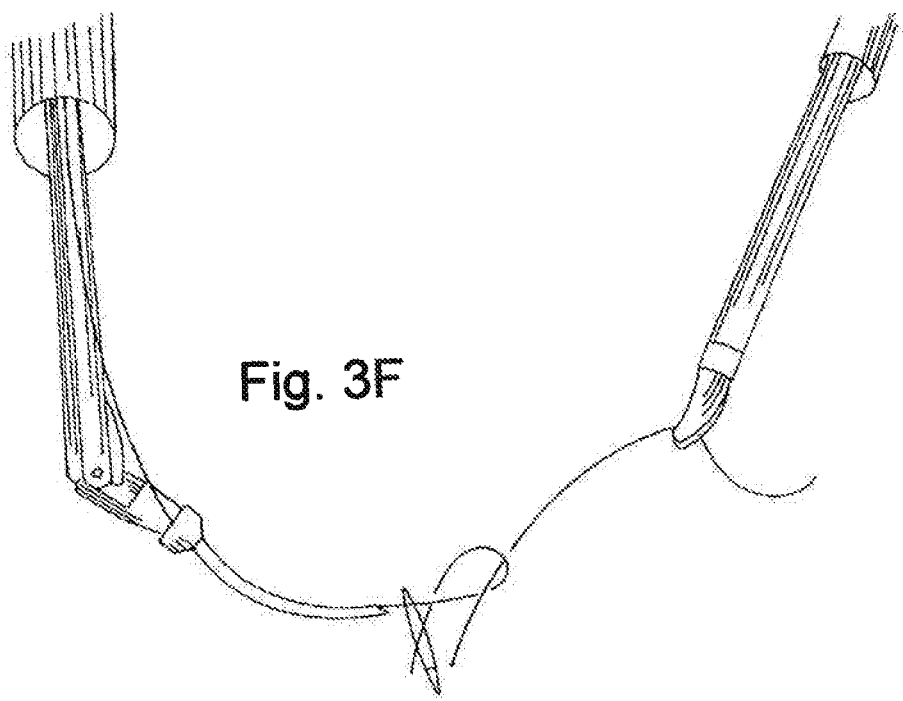
Fig. 3F
Fig. 3G

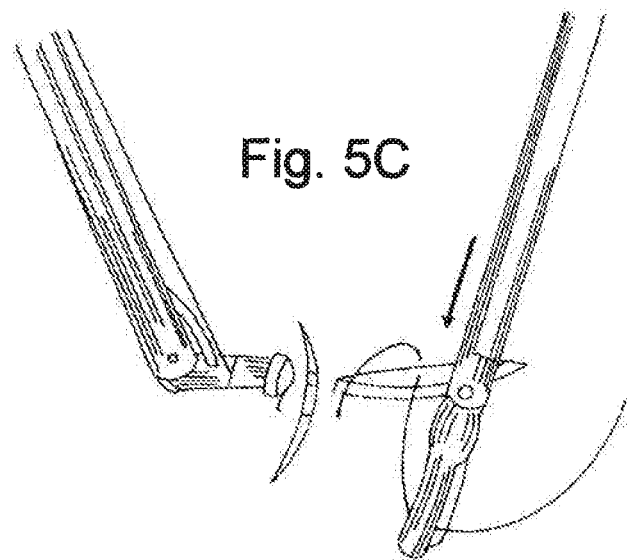
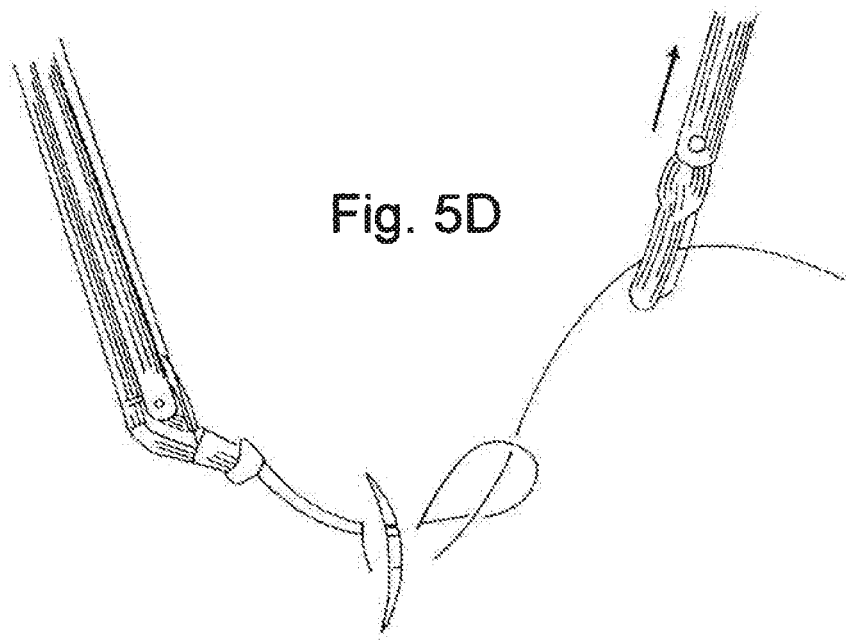

US 10,743,862 B1

LAPAROSCOPIC SUTURING DEVICE AND METHODS OF USE

CROSS REFERENCE TO RELATED APPLICATIONS

This application is a continuation of U.S. patent application Ser. No. 14/732,035, filed on Jun. 5, 2015, which is a continuation of U.S. patent application Ser. No. 11/418,050, filed on May 4, 2006.

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all rights whatsoever.

BACKGROUND OF THE INVENTION

1. Field of the Invention

This invention relates to a surgical device for suturing tissues more particularly during laparoscopic surgery but it can be used, after certain modifications, for various procedures in general and plastic surgery. In addition this device can be modified as a ligature passer for use in vascular surgery.

2. Description of Related Art

Suturing and knot tying constitutes a very important part in repairing surgical wounds but this task becomes more difficult when dealing with laparoscopic or endoscopic procedures. In many surgical procedures, suturing to approximate tissues is necessary for proper healing of lacerations and surgical incisions. This requires the formation and securing of knots and also the ligation of blood vessels to maintain the surgical field free from excess of blood and to reduce blood loss.

During laparoscopic procedures sutures can be tied manually either extracorporeally or intracorporeally. Extracorporeal knots are much easier to tie but requires the use of long strands of sutures and the use of a knot pusher which sometimes jams the knot making the procedure more tedious and difficult. On the other hand, intracorporeal knots requires a high level of expertise by the surgeon and may consume a lot of invaluable time. It is not uncommon for the tying of a simple knot to consume one hour and in many cases the knot is not tight enough becoming totally insecure.

BRIEF SUMMARY OF THE INVENTION

The present invention is aimed to solve the above mentioned problems by offering a simple device that keeps the suturing needle always attached to the instrument and is simple to operate. The needle never gets loose inside the body cavities and the formation of knots is easy to master. The knots are secured tight and will not get loose during the manipulation because they can be cinched in place in a safe manner.

It is further the object of the present invention to provide a several methods for inserting different kinds of sutures from single interrupted sutures to cinching mattress sutures and running sutures that can be used with advantage in laparoscopic and endoscopic procedures.

It is still a further object of the present invention to provide a thin shaft instrument that can be introduced through a 5 mm laparoscopic cannula.

It is still a further object of the present invention to provide an instrument that is much cheaper to produce than the current laparoscopic suturing devices.

It is still a further object of the present invention to provide a suturing device that uses a minimal amount of suture material.

In accordance with these and other objects, which will become apparent hereinafter, the instant invention will now be described with particular reference to the accompanying drawings.

BRIEF DESCRIPTION OF THE SEVERAL VIEWS OF THE DRAWINGS

FIG. 1 is a top perspective view of the preferred first embodiment of the laparoscopic suturing device;

FIG. 2A is a partial diagrammatical drawing of the preferred embodiment of the laparoscopic suturing device;

FIG. 2B illustrates the distal portion of the suturing device shown in FIG. 2A with the needle in a straight position;

FIG. 2C is a partial top view of the suturing device shown in FIG. 2A;

FIG. 2D shows the distal portion of the suturing device shown in FIG. 2C with the needle in a deployed position forming a right angle with the instrument's shaft;

FIGS. 3A to 3G illustrates the insertion a of a single interrupted suture using the laparoscopic suturing device in order to close a small surgical incision wherein, FIG. 3A shows the initial insertion of a single suture through the edges of the incision;

FIG. 3B shows the initial step for the formation of the first half hitch using the suturing device in combination with a semicurved tissue grasper.

FIG. 3C shows the formation of a triangular space using the instrument's needle and the two ends of the thread;

FIG. 3D shows the grasper PUSHING the free end of the suture through the previous triangular space;

FIG. 3E shows the same grasper pulling the end of the suture to complete the formation of a half hitch;

FIG. 3F shows the tightening of the first half hitch by pulling on the suture with the suturing device and the tissue grasper;

FIG. 3G shows the completion of the knot after using two more half hitches;

FIG. 5C shows the grasper holding down the free end of the thread and outside the arch;

FIG. 5D shows the same grasper pulling up the free end of the thread in preparation for the tightening of the cinching suture;

DETAILED DESCRIPTION OF THE INVENTION

Figure 3C:
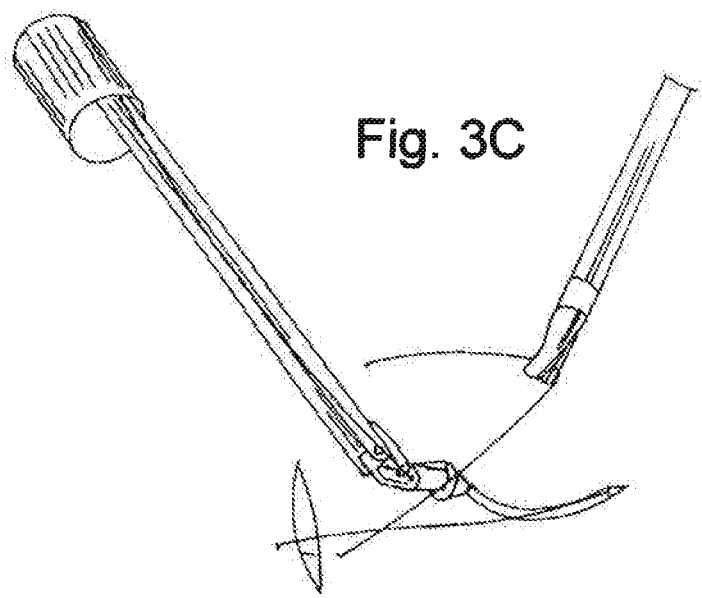

In reference to the drawings of FIGS. 1, and 2A-2D the following description is given to explain in detail the component parts of the first embodiment of the invention. FIG. 1 is a perspective view of a suturing device for use in laparoscopic surgery, generally referenced as 10, in accordance with the present invention. FIGS. 2A-B are side views of suturing device 10. Suturing device 10 is a surgical device for use in laparoscopic surgery, and is disposable and made of suitable metallic and plastic materials. Device 10 includes an ergonomic smooth handle 12 which is devoid of finger loops, and an elongated tubular shaft 14 that contains inside a connecting rod 15. Connecting rod 15 has its proximal end attached to a slidable deploying knob 18 by tightening of screw 17. Tubular shaft 14 is preferably generally cylindrical and has an outer diameter sized to enable insertion thereof within a cannula during a laparoscopic procedure. Accordingly, the entire structure of suturing device 10 which projects distally from handle 12 must be generally confined within a dimension corresponding generally to the outer diameter of tubular shaft 14 to be capable of insertion within the confines of a laparoscopic cannula. Said deploying knob slides back and forth in slot 24. Handle 12 is provided with an encasement 19 that supports a spool 20 that rotates on spool axis 22. Thread 27 from spool 20 passes through encasement channel 26 and is directed to a suturing hollow needle 38 through a needle channel 32 formed on a needle support or mount 34, whereafter thread 27 runs through the hollow interior of needle 38 and projects from an opening formed at the sharp end 39 of needle 38. It is important that the opening formed at the sharp end 39 of needle 38 is formed at the distal-most end of the needle such that initial threading of the needle is facilitated. Connecting rod 15 exits from tubular shaft 14 through opening 28 and is connected to a movable needle support 34 by means of an angulated end portion 37 of connecting rod 15. Movable needle support 34 rotates around pivot rod 30. Hollow suture needle 38 has a semi-curved shape and is attached to needle base 40 and the sharp distal end of the needle 39 is beveled similar to the beveled end of a hypodermic needle. It is important that the semi-curved needle 38 is longitudinally aligned with tubular shaft 14, and that the needle is confined within an extension of the outer bounds (illustrated by the broken lines referenced as "OD" in FIG. 2B), of tubular shaft 14, so as to fit within a laparoscope cannula when in use.

FIGS. 2C-D are top views of suturing device 10, and show ergonomic handle 12 with a generally oval shape and an elongated tubular shaft 14 that contains a connecting rod 15, which at its proximal end 16 is attached to deploying knob 18 by means of screw 17. The encasement 19 for spool 20 forms part of the handle 12 and is provided with two holes 21 to accommodate spool axis 22. Spool thread 27 passes through channel 26 and is directed to needle channel 32 to continue its way out through beveled opening 42 at the sharp end 39 of needle 38. The distal end of connecting rod 15 is linked to movable needle support 34 by means of an angulated end 37. There is a slant depression 41 around needle base 40 that forms a notch that is useful to hold back the thread while throwing half hitches. The movable needle support 34 rotates around pivot rod 30 and it may include a small sharp knife 43 that is of value to cut the thread after securing the knots. In FIG. 2D the suture needle has been deployed at 90 degrees to the left-hand side, relative to the shaft, by moving backwards the deploying knob 18. It is significant that the needle pivot to the left (i.e. counter-clockwise when viewed from above) as such pivotal movement positions the needle in an anatomical medial position whereby a right-handed surgeon is able to manipulate the needle using ergonomic clockwise and counter-clockwise movements of the right hand and wrist. This will allow the insertion of different types of sutures using a variety of suturing materials and according to the methods of use described here.

Methods of Use

The initial step in laparoscopic surgery is the establishment of pneumoperitoneum by insufflating the abdominal cavity with gas and then keeping the gas at a constant pressure. All the working instruments are inserted through especially designed laparoscopic cannulas that will keep the gas inside the abdominal cavity at a predetermined pressure in order to properly visualize the intra-abdominal organs.

The laparoscopic suturing device of the present invention can perform different types of sutures using intracorporeal knots that are easier to master as compared with the current methods. In addition the resulting knots are safer and more efficient because they can be cinched in place before additional half hitches are applied.

For instance, FIGS. 3A to 3G illustrates the insertion a of a single interrupted suture using the laparoscopic suturing device in order to close a small surgical incision but this type of suture is not recommended in laparoscopic surgery because it has the tendency to get loose before additional half hitches can be applied. FIG. 3A shows the initial insertion of a single suture through the edges of the incision and FIG. 3B shows the initial step for the formation of the first half hitch using the suturing device in combination with a semi-curved tissue grasper.

Figure 3D:
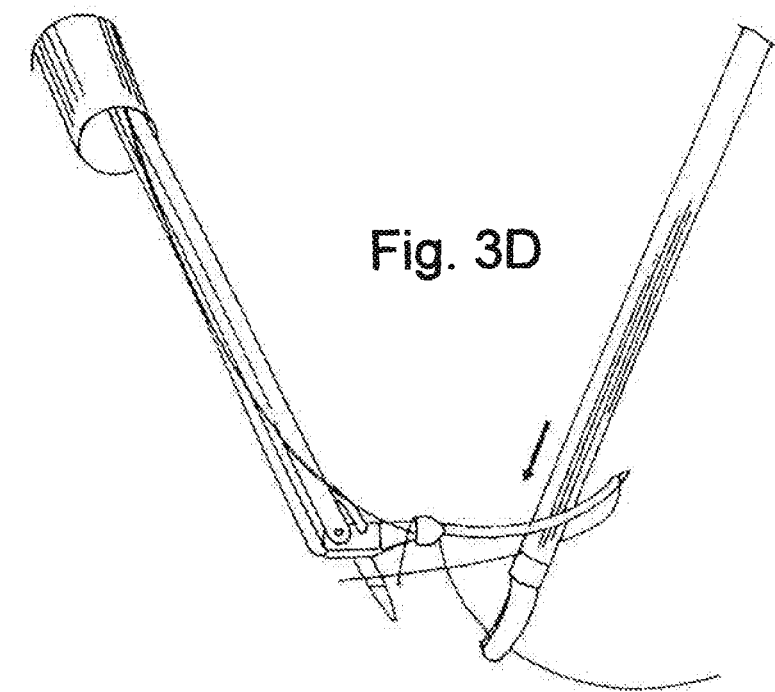

The following figures will describe in detail the steps needed for the formation of a single interrupted suture. FIG. 3C shows the formation of a triangular space using the instrument's needle and the two ends of the thread. FIG. 3D shows the grasper PUSHING the free end of the suture through the previous triangular space. FIG. 3E shows the same grasper pulling the end of the suture to complete the formation of a half hitch. FIG. 3F shows the tightening of the first half hitch by pulling on the suture with the suturing device and the tissue grasper. FIG. 3G shows the completion of the knot after using two more half hitches.

Figure 4A:
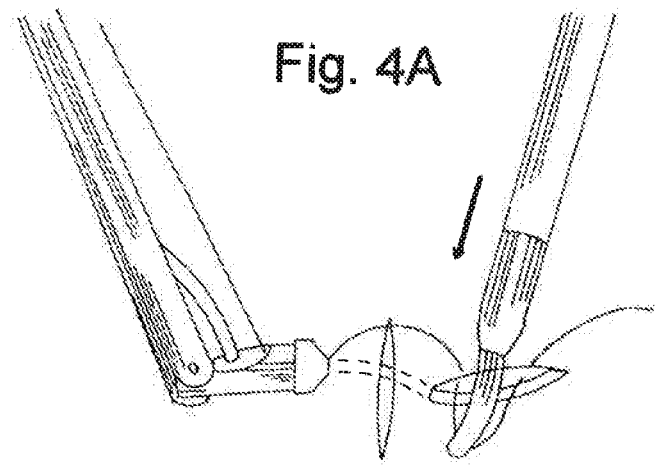
FIG. 4A shows the initial insertion of a single suture through the edges of the incision.
Figure 4B:
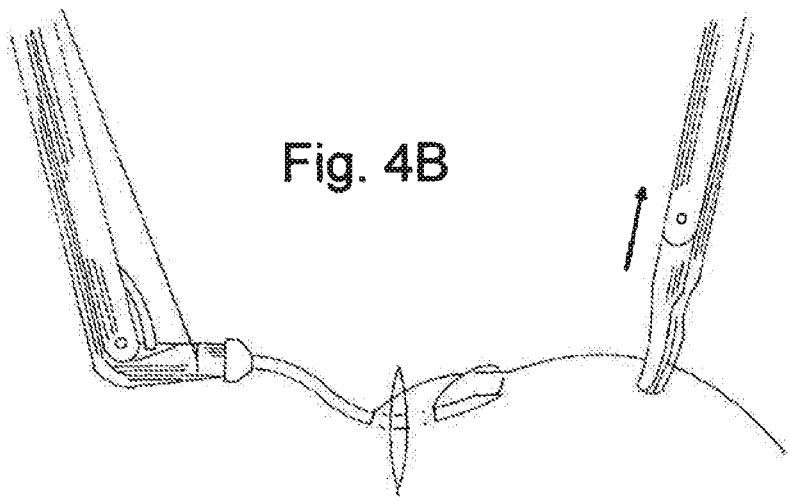
FIG. 4B shows the initial step for the formation of the first half hitch using the suturing device in combination with a semicurved tissue grasper.
Figure 4C:
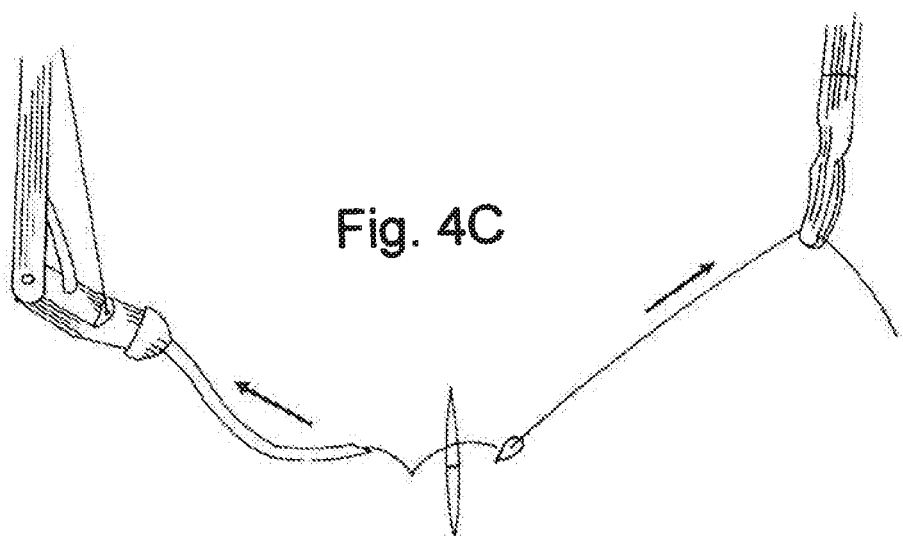
FIG. 4C shows the suturing device and the grasper pulling in opposite direction to tighten up the cinching suture.
Figure 4D:
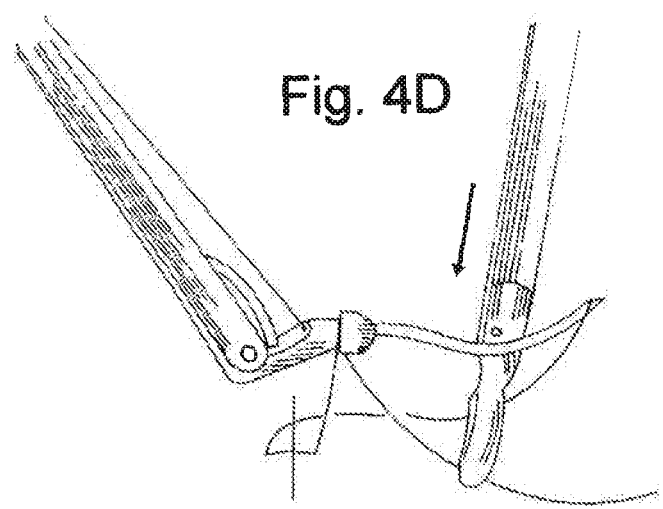
FIG. 4D shows the grasper PUSHING the free end of the thread through the triangular space formed by the needle and both ends of the thread.
Figure 4E:
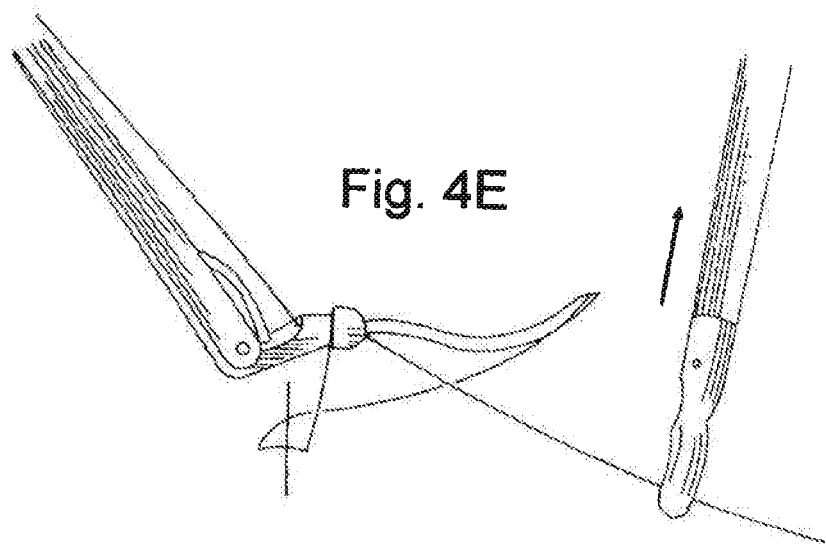
FIG. 4E shows the grasper pulling out the free end of the thread in preparation for tightening of the cinching suture.
Figure 4F:
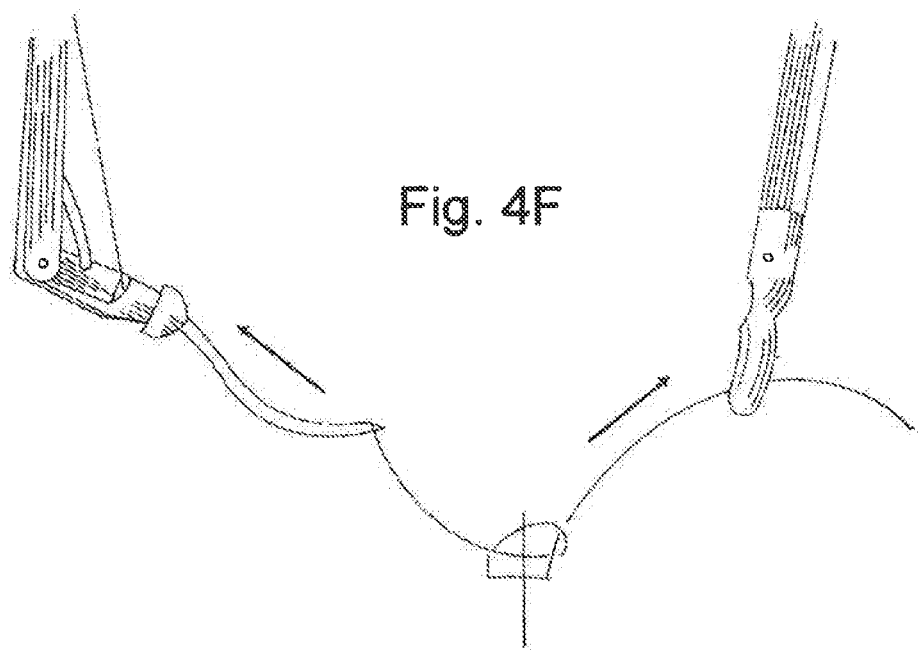
FIG. 4F shows the tightening of the cinching suture by pulling on the free end and the proximal portion of the thread.
Figure 4G:
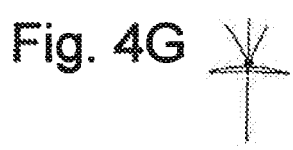
FIG. 4G shows the completed cinching knot after using two or three half hitches.

As opposed to the single interrupted suture, the cinching single suture is more secure and is very useful when tying tissues under tension such as the wrapping of the stomach around the esophagus during in the Nissen fundoplication. The following figures will illustrate the preferred method of use. FIG. 4A shows the first step for the formation of a single cinching suture by pushing the tissue grasper holding the free end of the thread through the arch formed between the curved portion of the needle and the proximal portion of the thread. FIG. 4B shows the grasper pulling the free end of the thread in order to begin tightening the cinching suture. FIG. 4C shows the suturing device and the grasper pulling in opposite direction to tighten up the cinching suture. FIG. 4D shows the grasper pushing the free end of the thread through the triangular space formed by the needle and both ends of the thread. FIG. 4E shows the grasper pulling out the free end of the thread in preparation for tightening of the cinching suture. FIG. 4F shows the tightening of the cinching suture by pulling on the free end and the proximal portion of the thread. FIG. 4G shows the completed cinching knot after using two or three half hitches.

The cinching horizontal mattress suture is similar to the single cinching suture but it is more practical since it requires only one knot for every two bites. Essentially it is a combination of a single interrupted suture and a cinching suture. The following figures will detail the method of use.

Figure 5A:
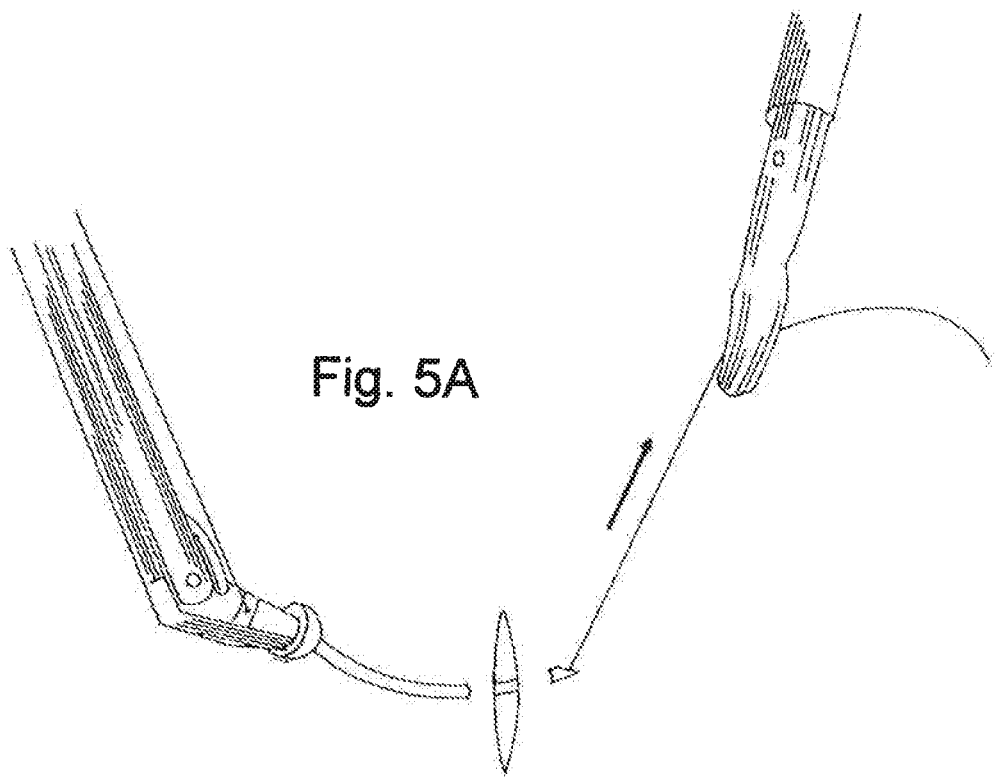
FIG. 5A shows the initiation of a cinching horizontal mattress suture as a single interrupted suture.
Figure 5B:
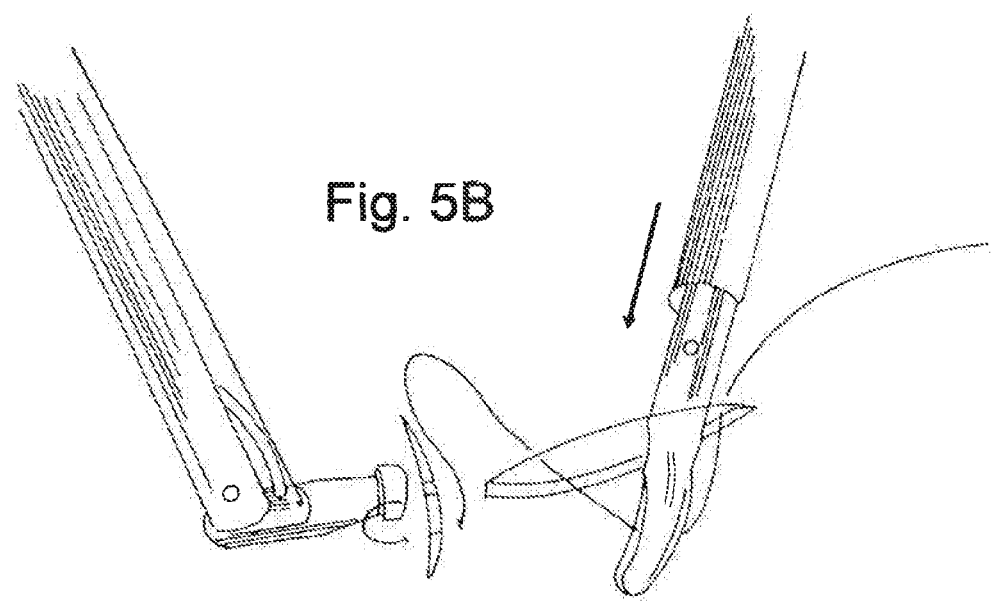
FIG. 5B shows the insertion of the suturing needle near the single suture and PUSHING the free end of the thread with the grasper through the arch formed by the curved needle and the proximal portion of the thread.
Figure 5E:
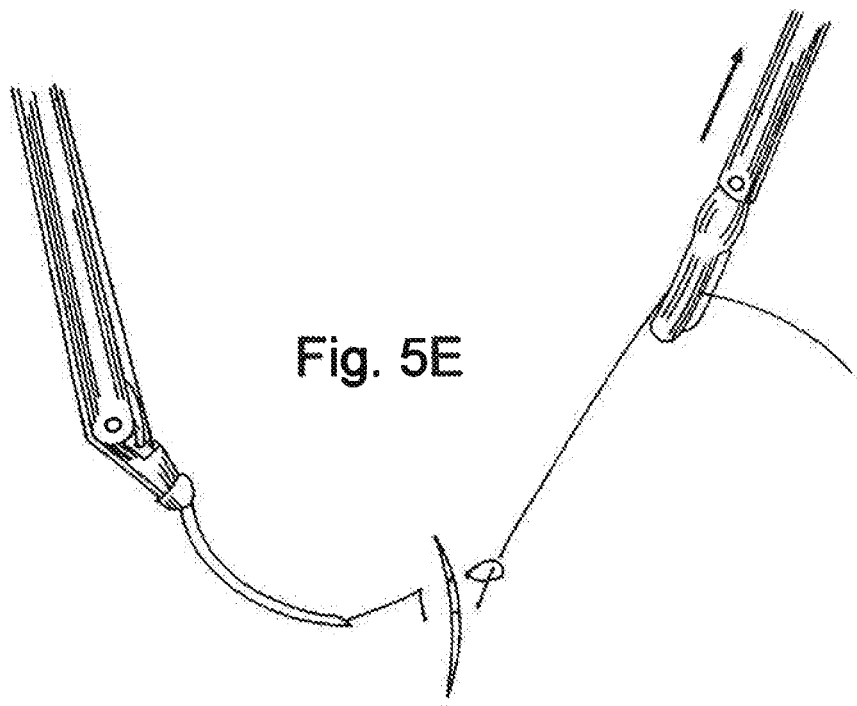
FIG. 5E shows tightening of the horizontal mattress suture by pulling on the thread with the grasper and suturing device.
Figure 5F:
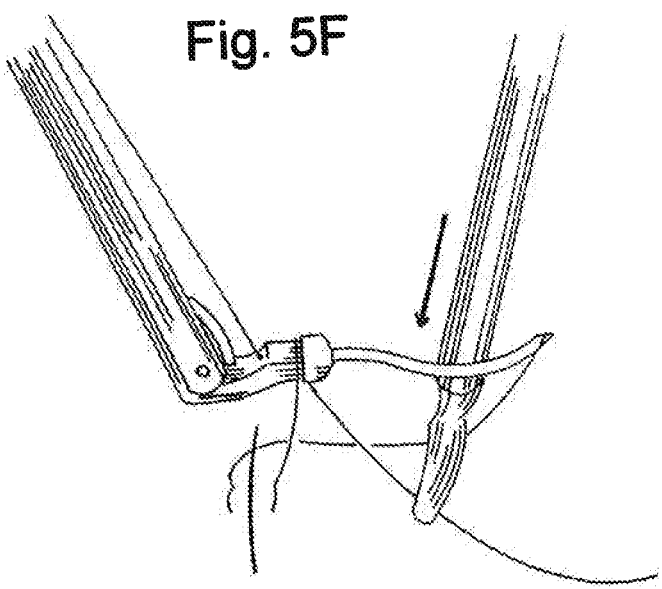
FIG. 5F shows the same grasper PUSHING the free end of the thread through the triangular space formed by the needle and the thread.
Figure 5G:
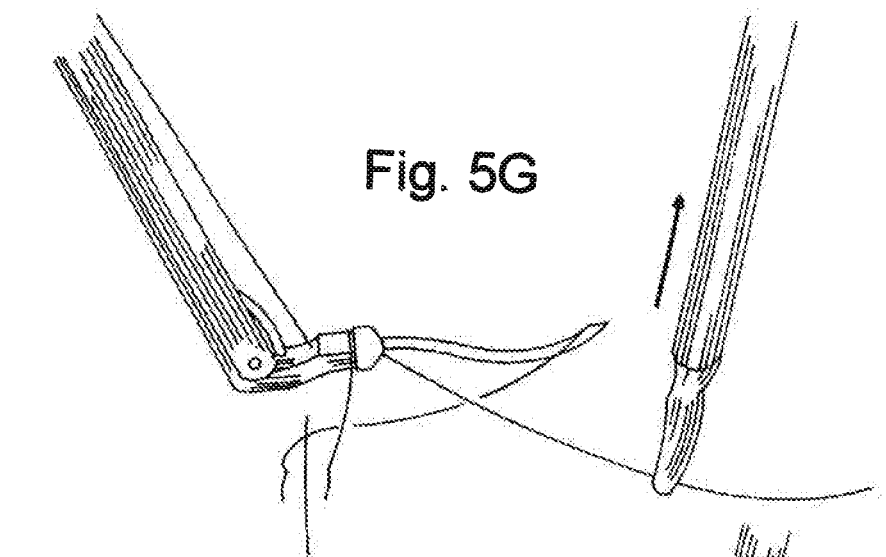
FIG. 5G shows the grasper holding the free end of the thread outside of the triangular space and pulling it upwards.
Figure 5H:
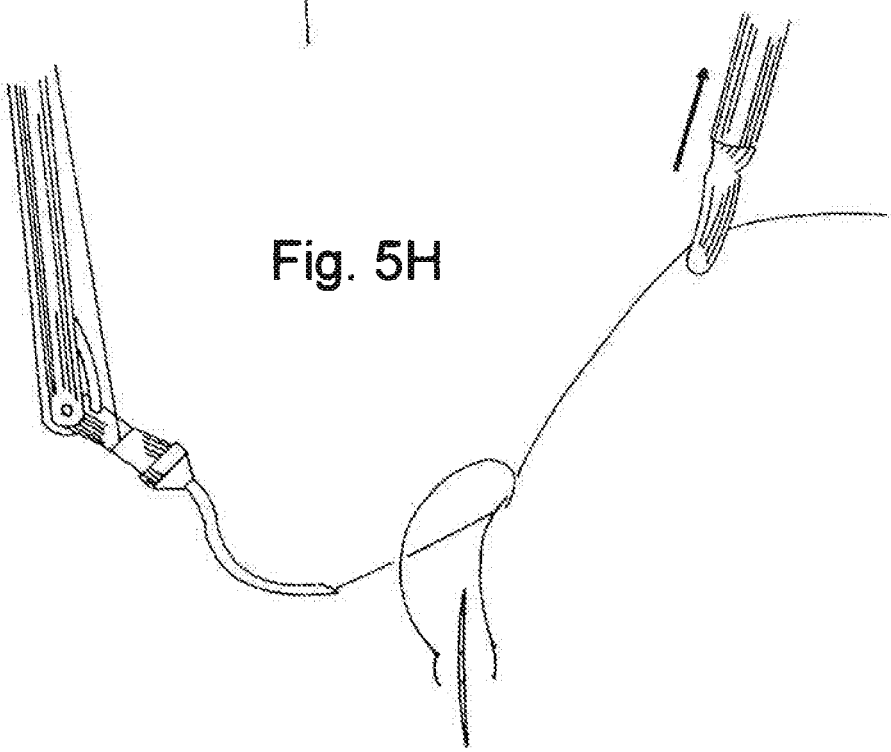
FIG. 5H shows the tightening of the cinching knot by pulling with the grasper and the suturing device.
Figure 5I:
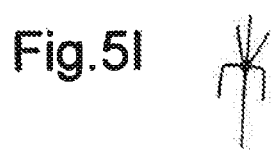
FIG. 5I shows the final knot after using two or three half hitches.

FIG. 5A shows the initiation of a cinching horizontal mattress suture as a single interrupted suture. FIG. 5B shows the insertion of the suturing needle near the single suture and pushing the free end of the thread with the grasper through the arch formed by the curved needle and the proximal portion of the thread. FIG. 5C shows the grasper holding down the free end of the thread and outside the arch. FIG. 5D shows the same grasper pulling up the free end of the thread in preparation for the tightening of the cinching suture. FIG. 5E shows tightening of the horizontal mattress suture by pulling on the thread with the grasper and suturing device. FIG. 5F shows the same grasper pushing the free end of the thread through the triangular space formed by the needle and the thread. FIG. 5G shows the grasper holding the free end of the thread outside of the triangular space and pulling it upwards. FIG. 5H shows the tightening of the cinching knot by pulling with the grasper and the suturing device. FIG. 5I shows the final knot after using two or three half hitches.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A laparoscopic suturing device comprising:
    a) a handle, having a top, a bottom, opposing left and right sides;
    b) a thread dispensing spool supported by said handle, said spool containing thread;
    c) a tubular shaft extending from said handle along a longitudinal axis to a distal end;
    d) said distal end including a movable needle support pivotally connected thereto;
    e) said needle support including a needle base;
    f) said needle support and said needle base defining a thread receiving aperture;
    g) a curved tubular needle permanently affixed to said needle base, said needle having a longitudinal axis and projecting from said needle base, said needle being hollow and having a tip defining an axial opening formed at a distal end thereof, and a proximal end opening aligned with said thread receiving aperture formed on said needle base, said thread passing external to said tubular shaft and passing though said needle support thread receiving aperture, through said needle base and completely through said needle, said thread exiting said needle through said axial opening at the distal end thereof, said needle support, said, needle base, and said, curved needle all being confined within a dimension that is less than or equal to an outer-diameter of said tubular shaft and axially aligned therewith to allow for insertion thereof through a cannula
    h) said handle including a deploying knob in slidable engagement therewith, said deploying knob connected to a connecting rod disposed within said tubular shaft, said connecting rod attached at a distal end thereof to said needle support:
    i) said needle support, pivotally movable from a first position wherein said needle support and said needle are generally aligned with said longitudinal axis to a second position wherein said needle support and said needle pivot approximately 90-degrees to the left-hand side so as to be generally perpendicular relative to said axis in response to slidable movement of said deploying knob; and
    j) a single knife edge disposed on said needle support on an opposing side of said needle base from said projecting needle.

2. A laparoscopic suturing device according to claim 1, wherein said knife edge falls within a plane defined by said tubular shaft and said movable needle support when said needle support is in said second position.

3. A laparoscopic suturing device according to claim 2, wherein said knife edge is disposed generally toward said handle when said needle support, is in said second position.

4. A laparoscopic suturing device according to claim 1, further defining a notch defined by said needle base and said needle support for holding thread while tying knots.

* * * * *